United States Patent
Weigel et al.

(10) Patent No.: US 7,112,273 B2
(45) Date of Patent: Sep. 26, 2006

(54) VOLUMETRIC FLUID BALANCE CONTROL FOR EXTRACORPOREAL BLOOD TREATMENT

(75) Inventors: William Weigel, York, ME (US); Daniel Call, Chicago, IL (US); Dennis Treu, Bedford, NH (US)

(73) Assignee: Nxstage Medical, Inc., Lawrence, MA (US)

(*) Notice: Subject to any disclaimer, the term of this patent is extended or adjusted under 35 U.S.C. 154(b) by 372 days.

(21) Appl. No.: 10/672,242

(22) Filed: Sep. 26, 2003

(65) Prior Publication Data

US 2005/0000868 A1  Jan. 6, 2005

Related U.S. Application Data

(60) Provisional application No. 60/414,322, filed on Sep. 27, 2002.

(51) Int. Cl.
*B01D 61/32* (2006.01)
*B01D 61/28* (2006.01)
*A61M 1/00* (2006.01)

(52) U.S. Cl. .................. 210/143; 210/90; 210/97; 210/101; 604/65; 604/67; 137/100

(58) Field of Classification Search ............... 210/90, 210/97, 101, 103, 134, 143, 646; 604/4.01, 604/5.01, 65, 67; 137/12, 98, 100
See application file for complete search history.

(56) References Cited

U.S. PATENT DOCUMENTS

| | | | |
|---|---|---|---|
| 4,108,574 A | 8/1978 | Bartley et al. | |
| 4,370,983 A | 2/1983 | Lichtenstein | |
| 4,464,172 A | 8/1984 | Lichtenstein | |
| 4,468,329 A | 8/1984 | Shaldon et al. | |
| 4,469,593 A | 9/1984 | Ishihara et al. | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,666,598 A | 5/1987 | Heath et al. | |
| 4,670,007 A | 6/1987 | Wheeldon et al. | |
| 4,702,829 A | 10/1987 | Polaschegg | |
| 4,713,171 A | 12/1987 | Polaschegg | |
| 4,728,433 A * | 3/1988 | Buck et al. | 210/646 |
| 4,765,888 A | 8/1988 | Barthe et al. | |
| 4,770,787 A | 9/1988 | Heath et al. | |
| 4,894,150 A * | 1/1990 | Schurek et al. | 210/101 |
| 4,894,164 A | 1/1990 | Polaschegg | |
| 4,899,057 A | 2/1990 | Koji | |
| 4,909,931 A | 3/1990 | Bibi | |
| 4,923,598 A | 5/1990 | Schal | |
| 4,950,395 A | 8/1990 | Richalley | |
| 4,997,570 A | 3/1991 | Polaschegg | |
| 5,211,849 A * | 5/1993 | Kitaevich et al. | 604/5.04 |
| 5,247,434 A | 9/1993 | Peterson et al. | |
| 5,277,820 A | 1/1994 | Ash | |
| 5,344,568 A | 9/1994 | Kitaevich | |
| 5,399,157 A | 3/1995 | Goux | |

(Continued)

*Primary Examiner*—John S. Kim
(74) *Attorney, Agent, or Firm*—Proskauer Rose LLP

(57) ABSTRACT

A method and device for adjusting a volumetric flow balancing system for an extracorporeal blood treatment system receives a pressure signal and calculates a compensation factor that is used to adjust the relative flow rates of the volumetrically balanced fluids. For example, in a hemofiltration system, the flow of waste and and replacement fluid may be balanced volumetrically. Ultrafiltrate may be pumped in a bypass circuit in such a system. The rate of ultrafiltrate flow may be adjusted by the compensation signal. The compensation signal may be empirically derived.

12 Claims, 9 Drawing Sheets

U.S. PATENT DOCUMENTS

| | | |
|---|---|---|
| 5,476,592 A | 12/1995 | Simard |
| 5,484,397 A | 1/1996 | Twardowski |
| 5,486,286 A | 1/1996 | Peterson et al. |
| 5,487,827 A | 1/1996 | Peterson et al. |
| 5,569,463 A | 10/1996 | Helmus et al. |
| 5,836,908 A * | 11/1998 | Beden et al. .................. 604/29 |
| 6,284,131 B1 * | 9/2001 | Hogard et al. .............. 210/143 |
| 6,579,253 B1 * | 6/2003 | Burbank et al. ............ 604/5.01 |
| 6,638,478 B1 * | 10/2003 | Treu et al. .................... 422/44 |
| 6,691,047 B1 | 2/2004 | Fredericks |

* cited by examiner

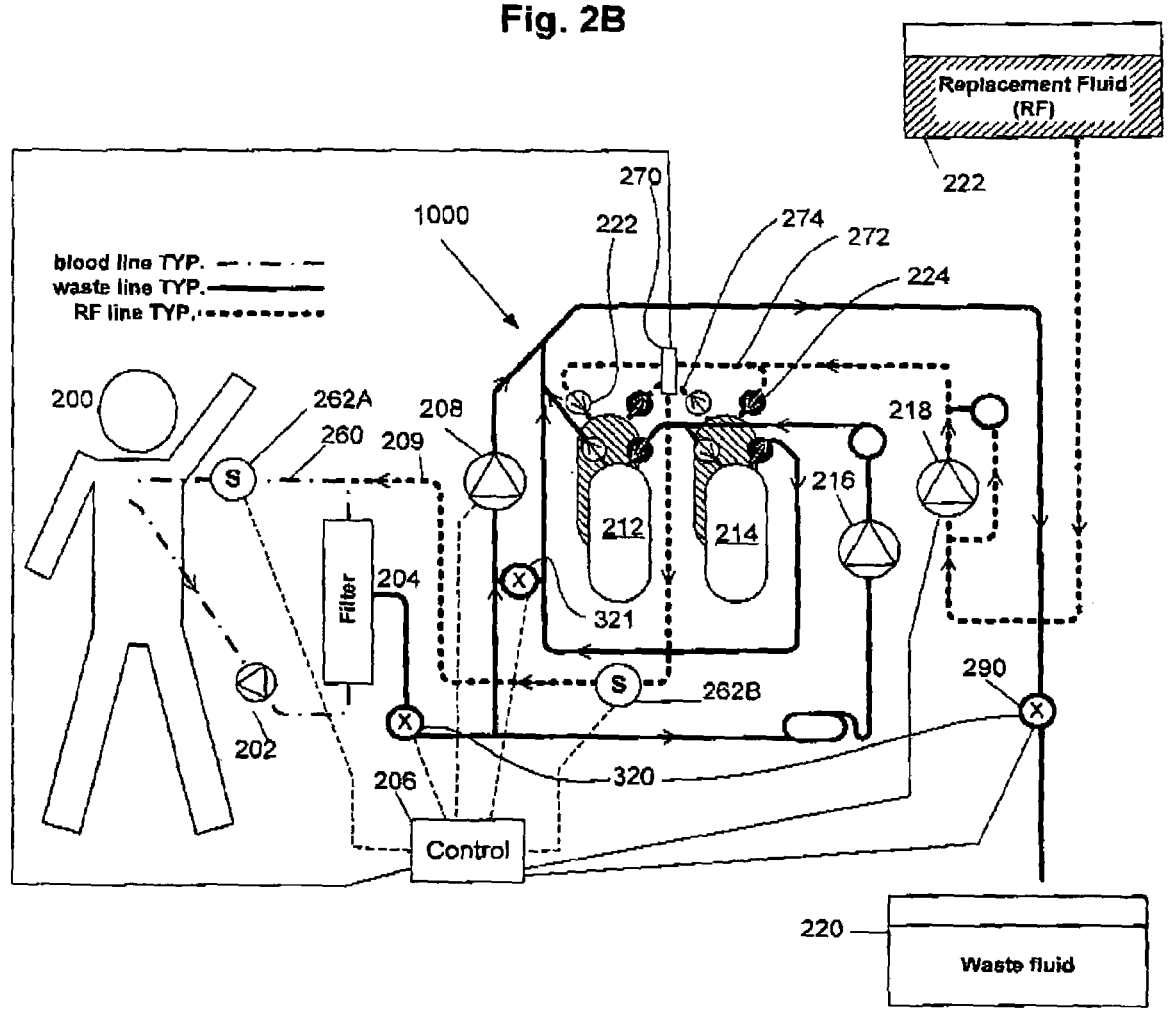

VOLUMETRIC FLUID BALANCE CONTROL FOR EXTRACORPOREAL BLOOD TREATMENT

REFERENCE TO RELATED APPLICATIONS

The present invention claims priority to U.S. patent application Ser. No. 60/414,322, filed Sep. 27, 2002 and entitled "Improvement In Volumetric Fluid Balance Control For Extracorporeal Blood Treatment".

BACKGROUND OF THE INVENTION

A core function of extra corporeal blood treatment systems (ECBT systems) such as hemodialysis, hemofiltration, hemodiafiltration, apheresis, etc. systems is the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total volumes of fluid pumped into and taken off the non-blood side of a filter or dialysis are equal. To provide for a desired differential between the net volume removed/added and a perfect balance, a fluid bypass driven by a separate pump may be employed. For example, this may be an ultrafiltration ("UF") line drawing extra fluid from the waste side of a hemofilter before the waste stream enters the balancing mechanism.

It is important to maintain the fluid balance such that the amount of fluid added or removed from the patient is accurately controlled. However, all balancing systems are imperfect. In addition, many balancing systems, in order to provide ease of use and compactness, employ incremental volume, mass, or flow measurements that can accumulate error. Thus there is a perennial need in the art for higher accuracy in balancing systems.

SUMMARY OF THE INVENTION

A common problem with prior art balancing mechanisms is that they can be biased by off-design conditions. For example, mechanical influences such as compliance in the balance chambers, backflow in pinch valves, approximations in flow rate sensor calibrations, etc. in response to off-design pressure differences or flow rates can bias fluid balance mechanisms causing an inaccurate fluid balance to result.

The above problems persist despite attempts to ensure a high degree of accuracy. For example, quality controls help to ensure repeatability from machine to machine, balance chamber pinch valve loads help to ensure predictable valve operation, and rigid balance chambers minimize compliance. Additional prior art approaches include direct measurement of the volume flow entering and leaving the patient.

Among the off-design conditions that can bias fluid balance control is excessive pressure due to access flow deterioration. In an embodiment of the invention, a numerical model of the influence of venous pressure is derived by calibration based on precise flow measurements. The model is used to compensate for bias in the fluid balance system during operation by means of software used by a control processor.

In one embodiment a numerical calibration curve was developed, modeling a fluid balance compensation value to another measurable quantity. This results in the detectability of a fluid volume imbalance without a direct measurement of the fluid volume entering and exiting the apparatus. A control could employ this model to efficiently compensate for any imbalance based upon the predicted values.

In an embodiment of the present invention, an error rate in a net fluid transfer rate is modeled as a function of venous pressure. A software algorithm then calculates a fluid compensation value proportional to the measured venous pressure. This algorithm is referred to as Venous Pressure Ultrafiltration Compensation ("VPUC"). A control can use the VPUC algorithm to determine whether or not fluid compensation is necessary to correct a fluid imbalance. The control may determine which form of fluid compensation is most appropriately delivered based upon the current operating condition of the device. If a UF pump is used, the pump rate can be reduced by the control based upon a compensation rate calculated according to the VPUC algorithm. Of course, the sane control software may provide for volume to be added during treatment as well. If the UF pump is not operating, the Cumulative Net Fluid ("CNF") value, the total amount of fluid to be added or removed from the patient, can be reduced at the calculated compensation rate. Finally, if the UF pump is not operating, and the CNF value is not positive, periodic boluses can be delivered to the patient in an amount equivalent to the desired compensation rate accumulated over time.

BRIEF DESCRIPTION OF THE DRAWINGS

FIG. 2a and 2b are more detailed schematic diagrams of a hemofiltration system.

DETAILED DESCRIPTION OF THE PREFERRED EMBODIMENTS OF THE INVENTION

A volumetric balance control mechanism may be implemented in a hemofiltration device. For the sake of illustration, the invention is discussed as applied to a particular hemofiltration system as described in patent application Ser. No. 09/513,911, entitled "Synchronized Volumetric Fluid Balancing Systems and Methods," filed Feb. 25, 2000, U.S. Pat. No. 6,638,478, the contents of which are hereby incorporated by reference as if fully set forth in their entirety herein. However, it should be understood that the discussion in this context is not intended to be limiting of the control mechanism and method of the invention as will be readily understood by persons of ordinary skill in the art.

Figure 1:
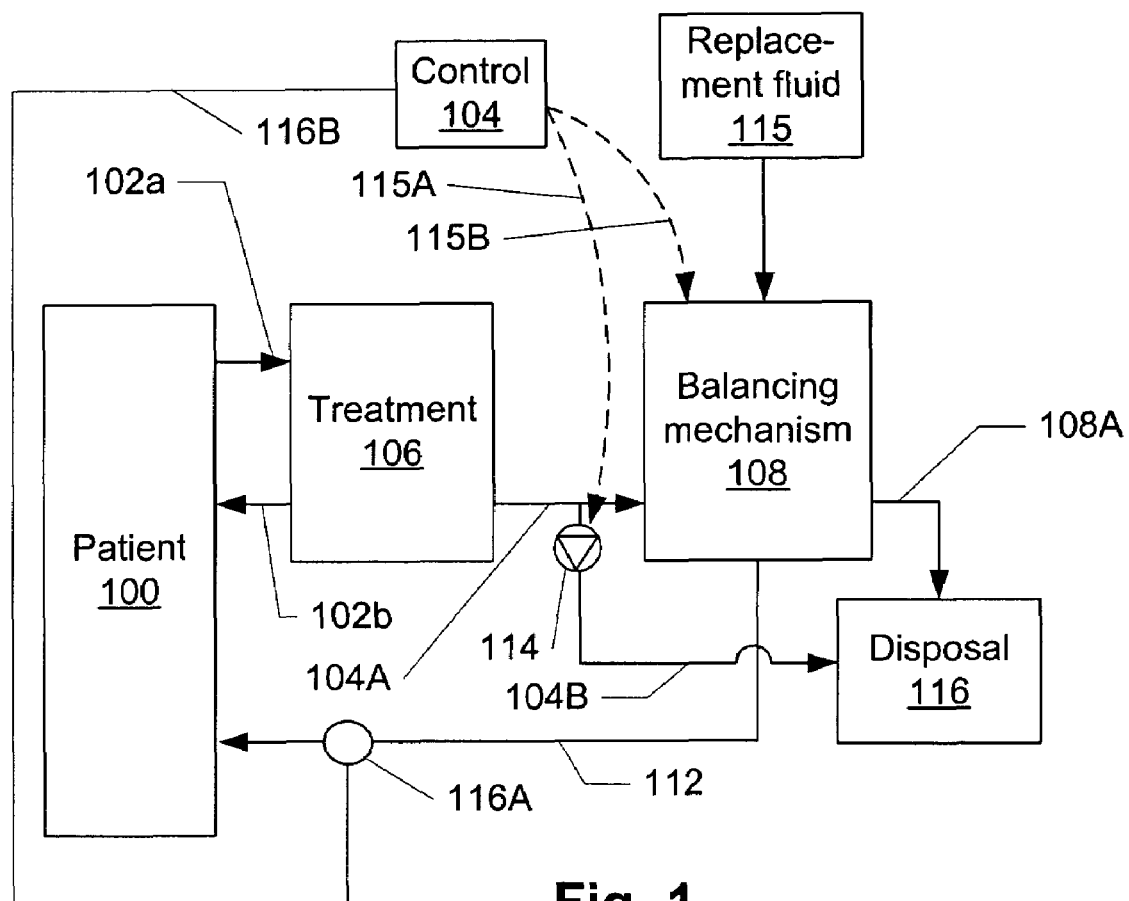
FIG. 1 is a figurative diagram of a hemofiltration system.

FIG. 1 illustrates a hemofiltration apparatus employing the present invention. Blood flows from the patient 100 through an arterial line 102a and returns blood to the patient via a venous line 102b. Waste is drawn through a waste line 104B from a treatment device 106 (conventionally, a filter) and sent to a disposal channel 116. The removal of waste 104 tends to reduce the volume of the blood so a balancing mechanism 108 restores this volume before returning the blood to the patient by adding replacement fluid to a venous line 102b. The balancing mechanism 108 maintains hydrostatic balance by adding precisely the same quantity of replacement fluid from a replacement fluid container 115, offset by a desired net ultrafiltrate prescribed for the treatment. Commonly, the excess over perfect fluid balance is drawn through an ultrafiltrate line 104B via a separate pump 114 under control of the controller 104.

The control 104 may also control the balancing mechanism directly without need for a separate ultrafiltrate line 104B by biasing the balancing mechanism such that the net ultrafiltrate volume is achieved over the course of treatment. These options are illustrated by control signal lines 115A and 115B. The data used to perform such ultrafiltrate control may be stored internally by means of a memory (not shown) for a programmable processor-based controller (not shown) or by means of a mechanical configuration (also not shown) adjusted before treatment. To further refine its ability to control ultrafiltrate levels, the control 104 may also adjust an effective control point responsively to a model of fluid balance error as a function of a measurable quantity, such as venous pressure, for example as measured by means of a pressure sensor 116A sending a continuous output signal 116B to the controller. The volume of replacement fluid 115 sent to the patient 100 can then be reduced or increased as indicated by the model.

Figure 2A:
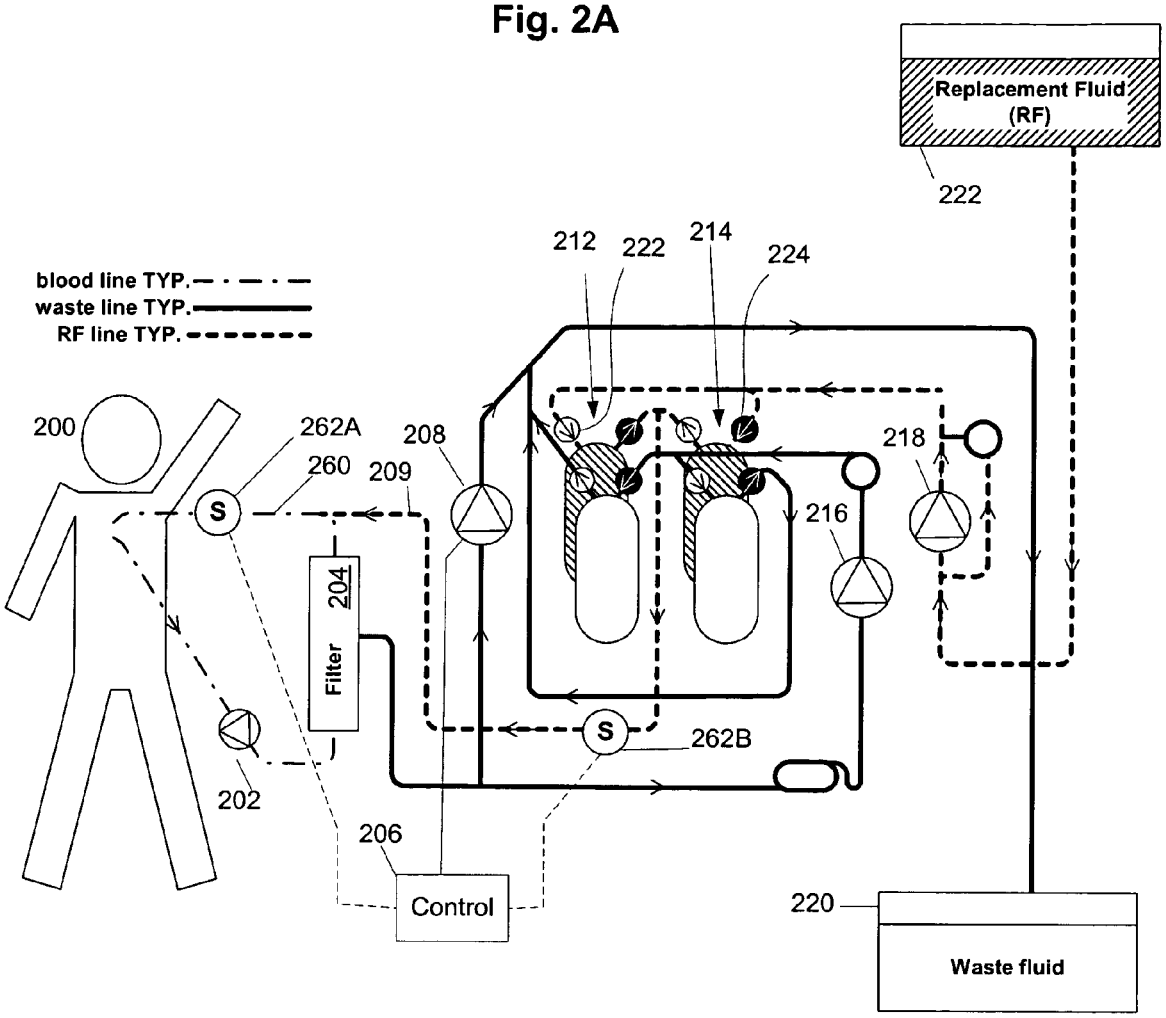

FIG. 2 is a diagram of a preferred embodiment hemofiltration apparatus employing the present invention. Blood is drawn from the patient 200 by a blood pump 202. The blood passes through a filter 204 and waste is extracted by a waste pump 216 from a waste side of the filter 204. Two balancing chambers 212, 214 each include a waste side (represented by the unshaded oval) and a replacement fluid side (represented by the shaded oval). As waste is fed into the waste side of each chamber, replacement fluid is forced out the other side. Each pair displaces replacement fluid at the same rate as waste fluid is drawn out of the patient. At any one time, only chamber 212 or 214 performs this function while the other chamber is reset by flowing replacement fluid into the replacement fluid side forcing waste fluid out of the waste fluid side. To accomplish this, two sets of valves are used, one set represented by black circles such as the one indicated at 224 and one set represented by white circles for example as indicated at 222. At any one time, only one set is open and the others are closed. Thus, at one time, all the valves represented as black circles (224 typ.) are open while all the valves represented as white circles (222 typ.) are closed and at other times, vice versa.

The operation of the pumps 216 and 218 cause RF to fill the replacement fluid side of one balancing chamber 212, 214, thereby forcing waste out of the other side while waste fluid fills the waste side of the other balancing chamber (212, 214) forcing replacement fluid out of the replacement fluid side. Thus, waste continuously flows from the filter, through the balancing chambers 212, 214, to a disposal channel 220 while replacement fluid flows from a replacement fluid source 222 through the balancing chambers 212, 214 into the venous return line 260 and into the patient. This process is described in the patent incorporated by reference above.

The ultrafiltration pump 208 functions as a partial bypass of the circuit that includes waste balancing chambers 212, 214, diverting waste before it displaces replacement fluid 222 to be sent to the patient, thereby reducing the volume of replacement fluid sent to the patient. This results in a net loss of fluid volume from the patient. As will be recognized by those of skill in the relevant arts, the above is one of a variety of different mechanisms. The repeated operation of valves and pressurization of fluid chambers attending the operation of such a balancing mechanism may cause cumulative error in the fluid balancing when conditions vary. For example, if a high-pressure head is experienced in the replacement fluid line, the displacement efficiency of the apparatus may be diminished or otherwise altered depending on materials and other design details.

A sensor 262A may be configured to measure pressure, from which a bias tending to affect the fluid balancing accuracy of the balancing chamber system described above may be derived. As indicated, the pressure sensor may be advantageously located to measure venous-line 260 pressure. A model of the impact of the pressure may be obtained from experimental calibration of the system by operating at various simulated venous line 260 pressures and measuring the effect on fluid balance. The experimental data may be readily transformed into a "curve fit" or linear approximation, allowing a controller 206 to adjust a control signal operating the ultrafiltration pump 208 to compensate such that the effect of the bias is effectively eliminated. In one embodiment, a sensor 262a is configured to measure venous pressure on the venous (return to patient) line and in another, the pressure in the replacement fluid line 209 feeding the venous line 260.

Referring now to FIG. 2B, in another embodiment, a differential pressure sensor 270 may be located to measure pressure difference between the replacement fluid inlet 272 side of the balancing chambers 212, 214 and the outlet side 274 of the balancing chambers 212, 214. The differential sensor 270 sensor could also be employed together with the other sensors and the inputs combined according to desired rules to provide compensation.

Additional sensor configurations could be internal or external to the patient, manual or automatic. The sensors could also be configured to measure a quantity from which pressure may be derived indirectly, for example, torque on the replacement fluid 216 pump shaft or the current on an independent motor driving the replacement fluid pump. Another source of a compensation signal may be relative changes in the pump speed to measured flow rate. Although flow rates are notoriously difficult to measure accurately, in a given configuration, relative changes in flow rate may be measured more precisely. When changes in the flow through the venous line 260 adversely affect throughput in the balancing mechanism, a shift in the ratio of flow rate, measured relative to pump speed, may be indicated by a suitable arrangement of sensors. Yet another example is a sound signature caused by intermittent backflow that may attend undesirable changes in volumetric efficiency. Identifying such a murmur may be done by applying an acoustical signature to a network classifier such as a Bayesian network, or neural network trained to recognize such a signature.

The control 206, in response to one or more signals as discussed above, may generate a control signal controlling the speed of the ultrafiltrate pump to compensate for any errors in the balancing process. Alternatively, the control signal may adjust some other mechanism for controlling the departure from perfect balance the effects the prescribed ultrafiltration rate.

In another embodiment of the present invention, the inventive control system is used in a hemodialysis machine.

Figure 3:
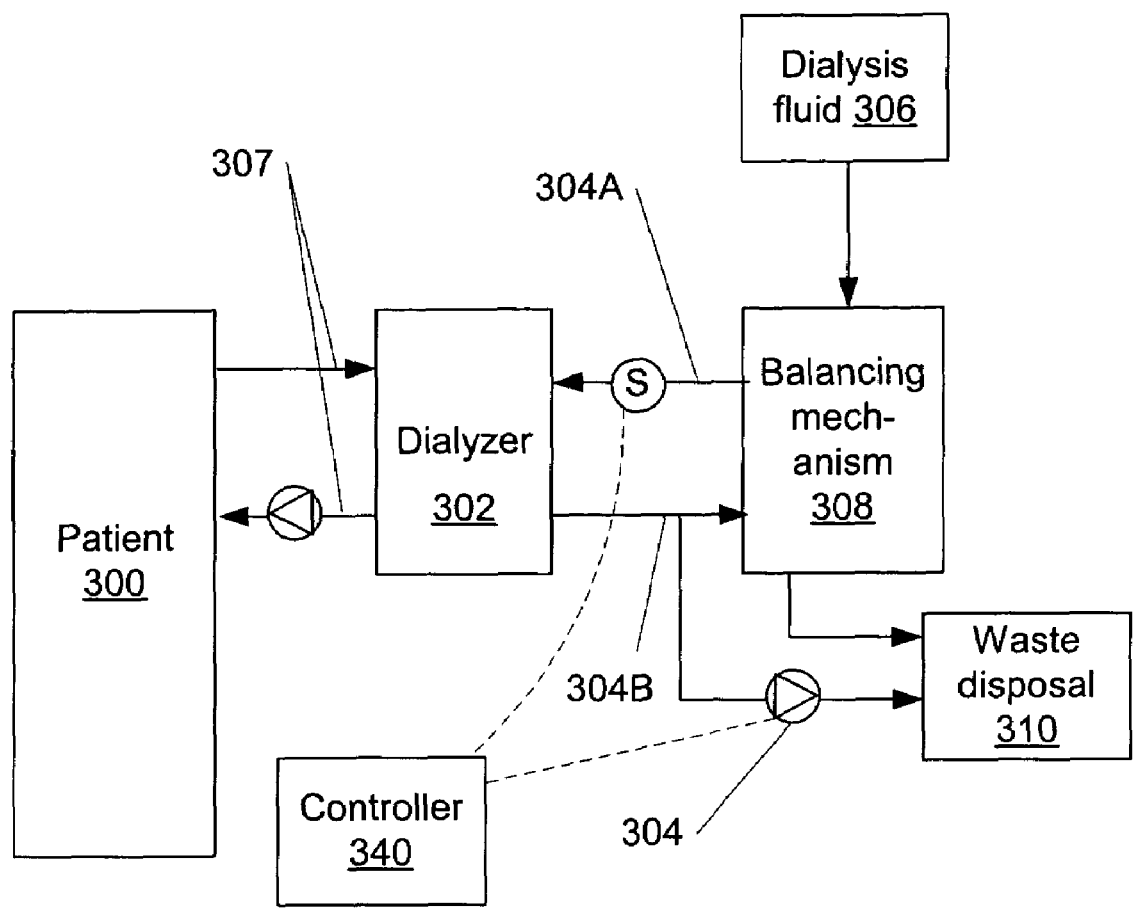
FIG. 3 is a figurative diagram of a hemodialysis system.

An example of a hemodialysis machine is shown in FIG. 3. The patient's 300 blood continuously circulates throughout a dialyzer 302. The configuration is similar to that of a hemofiltration system as illustrated in FIG. 1 except that dialysis fluid is circulated through the dialyzer 302 so there is stream of fresh dialysis fluid 304A and a stream of spent dialysis fluid 304B, which are maintained in balance by the balancing mechanism 308. The spent fluid is then sent to a disposal channel 310. An ultrafiltrate pump 304 pumps dialysis outside the balancing mechanism 308 thereby biasing the flow depending on the rate and configuration of the balancing mechanism 308. In this embodiment, the inventive control method can be used to compensate, for example, for off-design conditions in such a process by compensating in response to off-design pressure levels in the filter.

Figure 4:
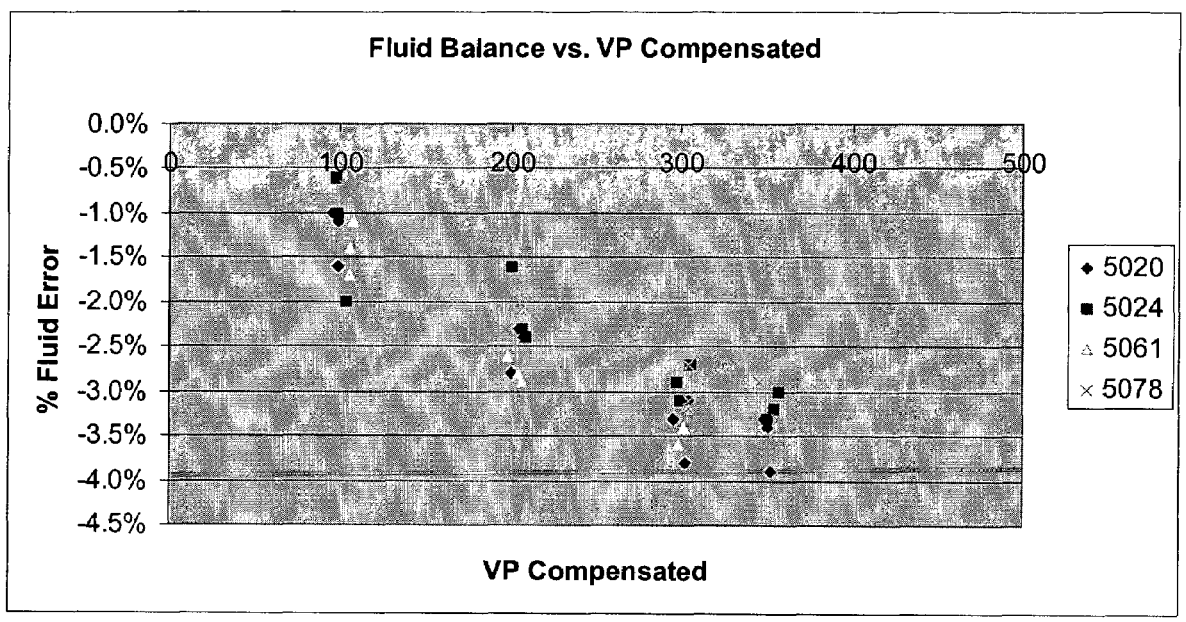
FIG. 4 is a diagram of VFMS Error as a function of Venus Pressure.

In an exemplary embodiment, a linear approximation of fluid balance error as a function of the venous pressure was derived experimentally by way of a series of tests. The results of these tests are shown in FIG. 4. First, mechanical adjustments were made to four hemofiltration machines 5020, 5024, 5061, and 5078 to optimize repeatability. A study of these four devices was then performed to quantify the impact of fluid balance of variations in pressure at the venous side fluid outlet. This data was then used to generate a series of linear approximations of the fluid balance error. In operation, the linear approximation may is used to counter-bias the ultrafiltration rate to improve off-design fluid balancing performance by programming a controller to compensate as required.

Figure 5A:
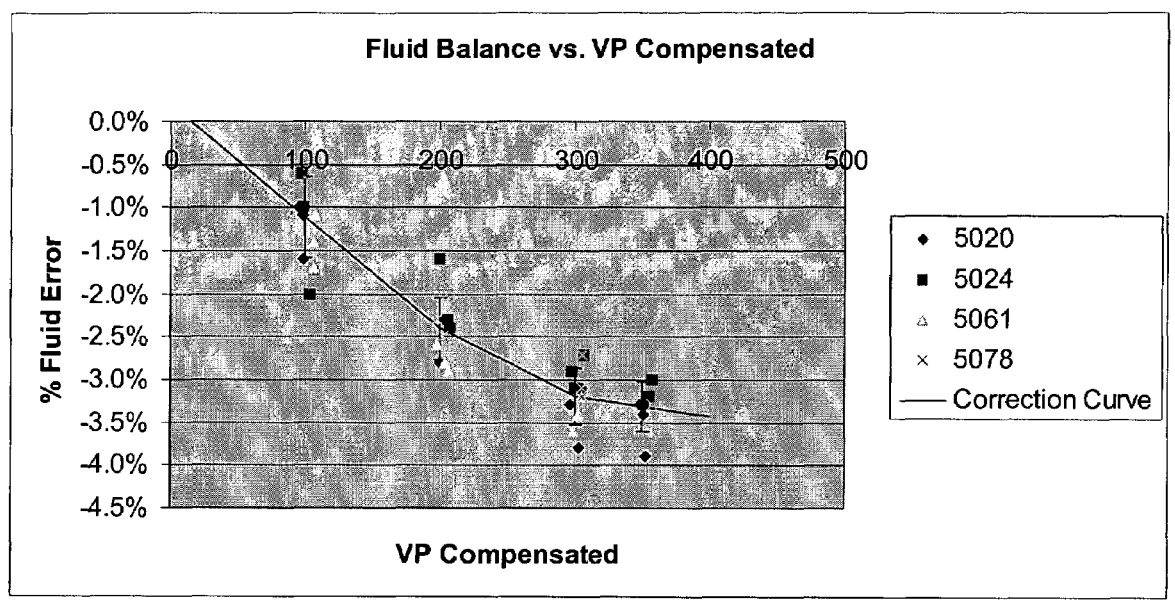
FIG. 5a and 5b are charts showing error data used to derive an error model with linear characteristics for use as a basis of compensating for bias in a balancing system.
Figure 5B:
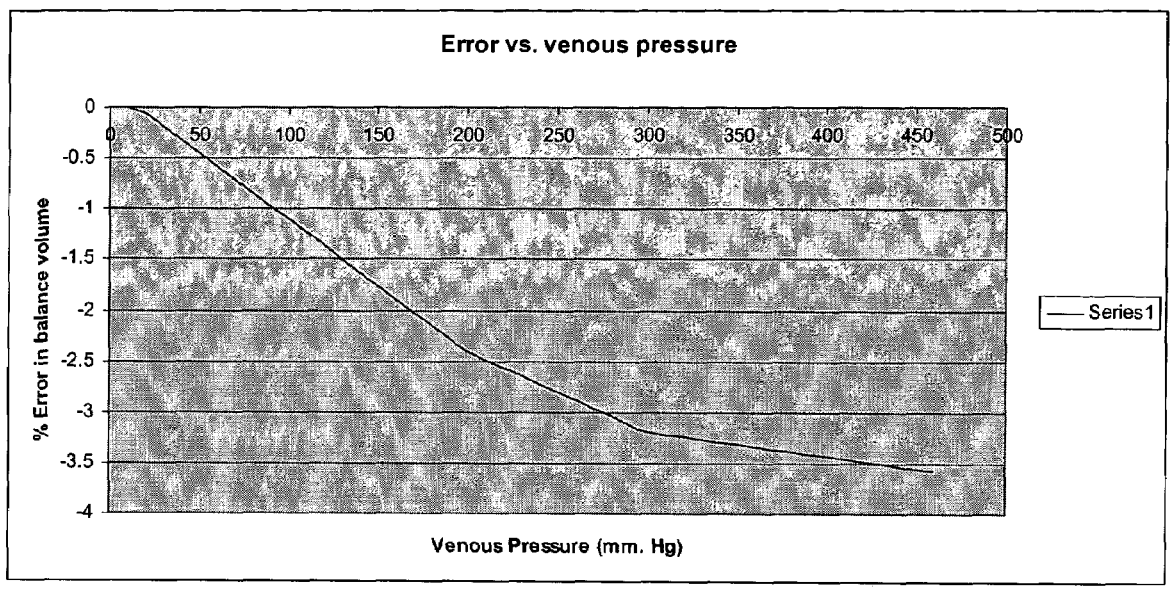

The hemofiltration machines were operated at a range of venous pressures (100–350 mmHg), with fluid balance information being collected from the patient over a 5-minute period. The balance error, while obviously nonlinear, has zones that are substantially linear. To simplify the algorithm, the balance error was approximated by a series of line segments, as shown in FIG. 5A. These four linear zones, or line segments, were captured in a single (piecewise continuous) correction function:

$$e(v) = 0 - \begin{cases} 0 & \text{for } v < b_l \\ m_l(v - b_l) & \text{for } b_l < v \leq b_m \\ m_l(b_m - b_l) + m_m(v - b_m) & \text{for } b_m < v \leq b_h \\ m_l(b_m - b_l) + m_m(b_h - b_m) + m_h(v - b_h) & \text{for } v < b_h \end{cases}$$

where
  $e(v)$=percentage error
  $v$=venous pressure
  $b_l$=low pressure inflection point
  $b_m$=middle pressure inflection point
  $b_h$=high pressure inflection point
  $m_l$=low pressure slope
  $m_m$=middle pressure slope
  $m_h$=high pressure slope The result of this equation, $e(v)$, is the percentage error rate of VFMS balance. The values of the 6 parameters were determined from the test data using a "least squares" method to minimize the sum of squared errors between the performance of the balancing mechanism, and $e(v)$. The following parameters were found to provide a good fit to the data:
  $b_l$=15 mmHg
  $b_m$=200 mmHg
  $b_h$=300 mmHg
  $m_l$=0.013%/mmHg
  $m_m$=0.0079%/mmHg
  $m_h$=0.0024%/mmHg The second and third inflection points ($b_m$, $b_h$) were constrained to 200 mmHg and 300 mmHg respectively. This results in a coefficient of determination ($r^2$) of 0.84. The resulting curve is shown in FIG. 5B.

The ultrafiltration rate can be adjusted based on the following formula, which indicates an offset from the commanded rate:

$$UFR_{new} = UFR_{old} - e(v) \cdot RFR$$

When $UFR_{old}$ is greater than $e(v) \cdot RFR$, $UFR_{new}$ remains positive and the pump continues to run at the new rate. If, however, $UFR_{old}$ is less than $e(v)RFR$, the VFMS imbalance is removing weight from the patient beyond the intentions of the operator.

The problem of extra removal present in the latter condition may be dealt in several ways. For example, if the CNF is positive, the $UFR_{new}$ is deducted from the CNF as if the ultrafiltration pump were running. This allows the balancing mechanism to remove the weight it has added, or will add, to the patient. If the CNF is already depleted and no further weight removal is desired by the operator, the patient now has a high likelihood of completing the treatment underweight. A bolus of replacement fluid can be delivered to compensate by manual infusion or by under automatic control. After the intended weight is fully removed, $UFR_{new}$ is added to a pending volume. After each VFMS check, the pending volume is delivered back in a bolus, effectively returning the weight removed since the last VFMS check. The pending volume collected after the final VFMS check is added to the Rinseback volume, bringing the patient into equilibrium at the end of therapy.

Referring to FIG. 2B, the bolus can be delivered automatically, for example, by short-circuiting a flow of waste fluid through the balance mechanism by closing valves 320 and opening valve 321 in a bypass to form a closed circuit that circulates waste fluid to pump replacement fluid. This may be done under automatic control by the control 206 for a number of cycles required the required bolus.

A verification study of two treatments was performed using the approach in the example illustration discussed above. During the first treatment in the study was the $V_P$ was 300 mmHg. The total error for this treatment was +1.0% of RF Volume; without VPUC, the data collected at 300 mmHg had a mean error of −3.18% ($\sigma$=0.33%). The corrected error was 12.7 $\sigma$ from the mean. The second treatment was run at VP=100 mmHg. The total error for this treatment was +0.4% of RF Volume; without VPUC, the data collected at 100 mmHg had a mean error rate of −1.13% ($\sigma$=0.47%). The corrected error was 3.7 $\sigma$ from the mean. VPUC successfully improved the fluid balance accuracy of balancing mechanism over the course of a treatment. Although this technical improvement has been optimized for the balancing mechanism, a similar approach will improve the fluid balance accuracy of other hemofiltration or hemodialysis machines.

It should be understood that the above venous pressure-based calibration equation procedure and results are discussed to illustrate how calibration can be used to derive a bias compensation function which may be implemented by a programmable processor or other means, such as a purely mechanical mechanism, for example using pneumatic controls with an analog pressure sensor driving it. Much more sophisticated methods may be used in practice and this example is presented for illustration only. A calibration curve could be generated based upon any quantity from which similar experiments could generate predictable fluid imbalance results.

Figure 6:
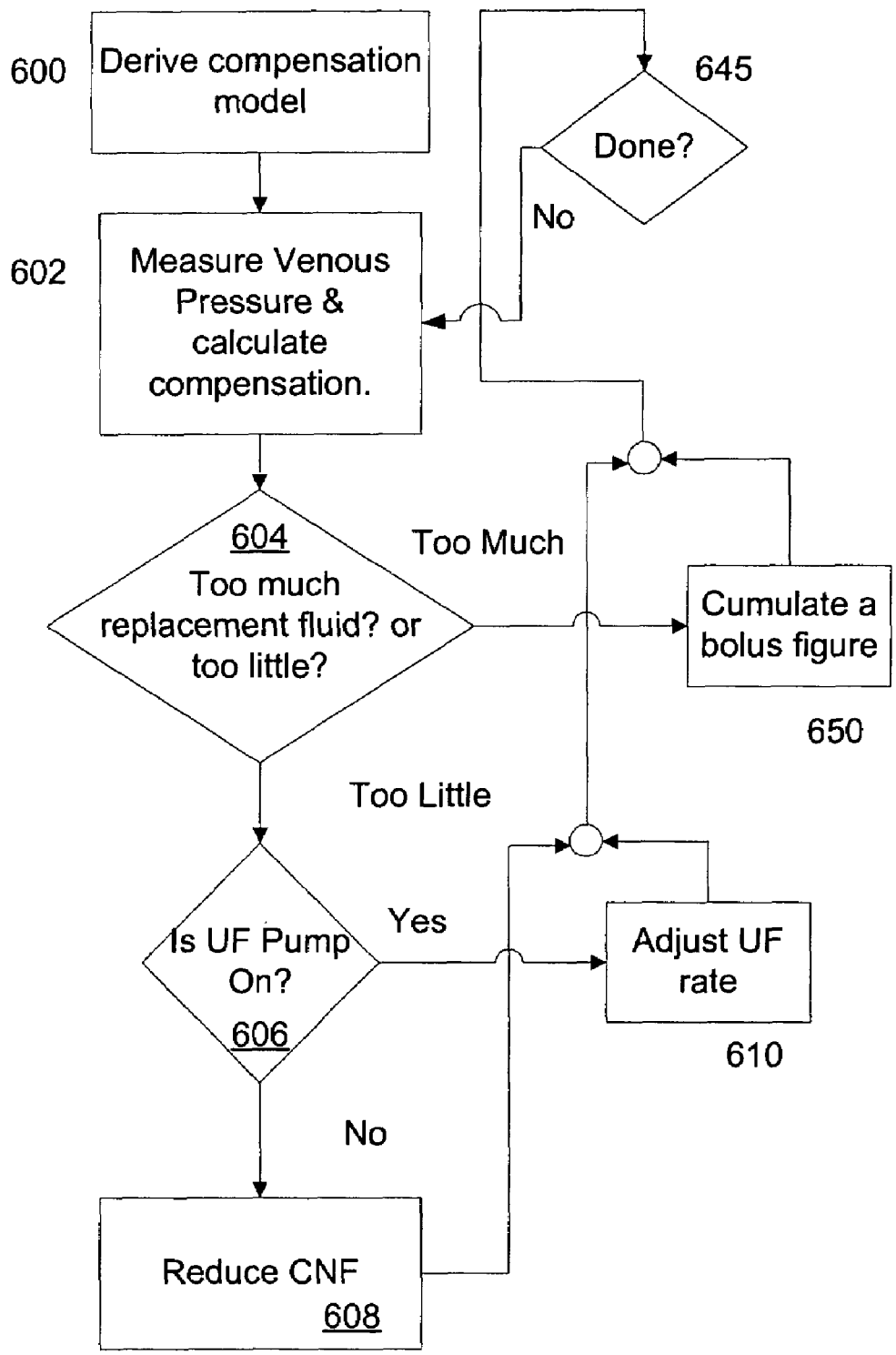
FIG. 6 is a flow chart to illustrate a control flow that may be used to implement features of the present invention.

FIG. 6 is a flowchart of one embodiment of the inventive methodology. The first step is the derivation of a model of fluid balance error 600 as a function of one or more input variables. The Venous Pressure will be measured next. 602. By comparing the venous pressure to the calculated error rate, a control signal can be generated which can compensate for any fluid imbalance. Effectively, the control indirectly measures the fluid imbalance through the direct measurement of another system property, in this case, venous pressure. Based on the measurement 600 and the model 602, the control determines whether too much or too little fluid is being added to the patient 604. If too little fluid is being delivered, so that the patient will finish treatment underweight, a bolus, or a series of boluses may be delivered 650. If too much fluid is present, such that the patient will finish overweight, and if the UF pump is on 606, the control can reduce the rate of the UF pump 610 little fluid. Otherwise, the CNF can be otherwise reduced 608. The process is then repeated until the treatment is complete 645.

In some situations it is undesirable to calculate a compensation value based upon only a single measurement. If the measurement is incorrect, then the calculated compensation calculated will be in error. Mathematical modeling allows the generation of more reliable indicia from multiple sources, each of which alone might be less reliable than desired. In another embodiment of the present invention, a network model, for example a neural network, is employed to generate a more reliable compensation mechanism for fluid balance by leveraging multiple inputs relating to the system operation.

Figure 7:
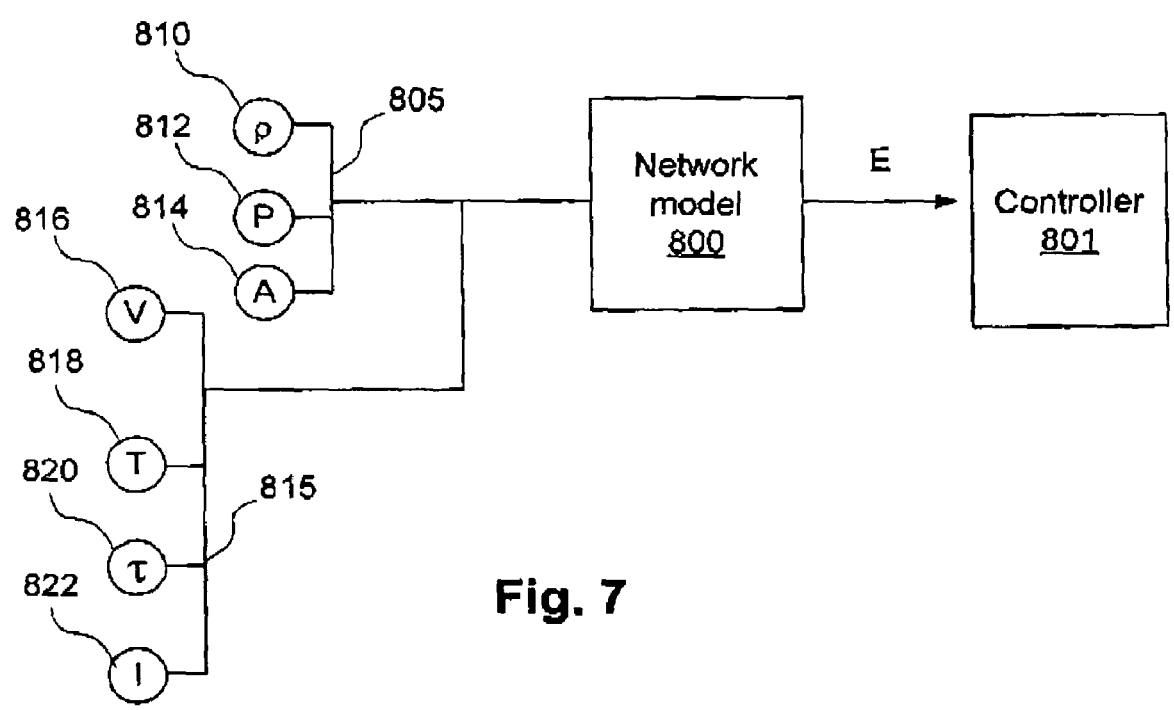
FIG. 7 is a figurative diagram of a control system employing a neural network or network model.

Referring to FIG. 7, a variety of inputs may be applied to network model 800 and the model 800 trained or otherwise programmed to combine these signals into a compensation signal E using the feedback of a calibration process exemplified by the sample process described above. Inputs that may affect the performance of the balancing mechanism include: fluid properties 805 such as density or conductivity 810 pressure or differential pressure, both indicated at 812, an audio signature (frequency spectrum where each frequency channel may be an independent component of the entire input vector) 814, fluid velocity 816, fluid temperatures or temperature rise (both indicated at 818) through the balancing mechanism, pump motor shaft torque 820, pump motor current draw 822, and others.

As this invention may be embodied in several forms without departing from the spirit of essential characteristics thereof, the present embodiment is therefore illustrative and not restrictive. The scope of the invention is defined by the appended claims rather than by the description preceding them. All changes that fall within the metes and bounds thereof are therefore intended to be embraced by the claims.

What is claimed is:

1. A device for balancing the flow of fluids in a blood treatment system, comprising:
   a balancing mechanism having inlets and outlets for a first flow of fluid that includes renal waste and a second flow of fluid including fluid to be infused into a patient;
   at least one pressure sensor configured to measure a pressure difference between at least one of said inlets relative to a respective outlet;
   the balancing mechanism employing a volumetric system that is subject to variation in relative flow volume rates due to variations in differences between respective inlet and outlet pressures of said first and second flows;
   said balancing mechanism configured to receive a compensation signal and adjust a balance between a ratio of said first flow to said second flow responsively to said compensation signal to maintain a correct fluid balance of the patient;
   a controller configured to generate said compensation signal responsively to at least one pressure measurement by said at least one pressure sensor, said at least one pressure measurement including at least one of said differences between respective inlet and outlet pressures of said first and second flows.

2. A device as in claim 1, wherein said controller configured to store a continuous control curve indicating a correspondence between experimentally determined error versus pressure, said compensation signal being derived from said pressure measurement responsively to said control curve.

3. A device for balancing the flow of fluids in a blood treatment system, comprising:
   a volumetric balancing mechanism having inputs and outputs for respective first and second fluid flows, at least one of said outputs being connected to a venous line of a blood circuit that returns blood to a patient;
   at least one pressure sensor in at least one of said venous line and said outputs for measuring venous pressure;
   a controller configured to calculate an error rate in a net fluid transfer rate as a function of a signal from said pressure sensor and further to generate a fluid compensation signal responsive to said error rate;
   wherein said volumetric balancing mechanism is configured to receive said fluid compensation signal and adjust a relative rate of said first and second fluid flows responsively thereto.

4. A device as in claim 3, wherein said first flaw is a waste flow from a blood filtering device.

5. A device as in claim 4, wherein said second flow is a replacement fluid flow.

6. A device as in claim 3, wherein said second flow is a replacement fluid flow.

7. A device for balancing the flow of fluids in a blood treatment system, comprising:
   a volumetric balancing mechanism having first and second flow paths with respective inputs and outputs, one of said flow paths being adapted for conveying a first fluid flow consumed during a blood treatment and the other of said flow paths being adapted for conveying a second fluid flow generated at least partly from said blood treatment;
   at least one pressure sensor configured to measure a pressure difference between at least one of said inputs relative to a respective output;
   a controller configured to calculate an error rate in a net fluid transfer rate as a function of a signal from said pressure sensor and further to generate a fluid compensation signal responsive to said error rate;
   wherein said volumetric balancing mechanism is configured to receive said fluid compensation signal and adjust a relative rate of said first and second fluid flows responsively thereto.

8. A device as in claim 7, wherein said first flow is a waste flow from a blood filtering device.

9. A device as in claim 8, wherein said second flow is a replacement fluid flow.

10. A device as in claim 7, wherein said second flow is a replacement fluid flow.

11. A device as in claim 7, wherein said relative rate affects a net fluid balance of a patient receiving treatment.

12. A device as in claim 11, wherein said treatment is a dialysis treatment.

* * * * *